(12) United States Patent
Cholewa

(10) Patent No.: US 6,425,998 B1
(45) Date of Patent: Jul. 30, 2002

(54) PROCESS FOR DETECTING IMPURITIES IN LIQUID METAL HEAT EXCHANGE FLUID IN HIGH HYDROGEN PERMEATION ENVIRONMENT

(75) Inventor: Donald Cholewa, Highland Park, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/511,211

(22) Filed: Feb. 23, 2000

(51) Int. Cl.⁷ .................. C10G 35/00; C10G 47/00; C10G 45/00; C07C 5/327
(52) U.S. Cl. .................. 208/133; 208/107; 208/108; 208/134; 208/142; 208/143; 208/DIG. 1; 208/209; 208/213; 585/407; 585/654
(58) Field of Search .................. 208/107, 108, 208/133, 134, 142, 143, DIG. 1, 209, 213; 585/407, 654

(56) References Cited

U.S. PATENT DOCUMENTS

| | | | |
|---|---|---|---|
| 3,731,523 A | 5/1973 | Vissers et al. ............ | 73/19 |
| 3,941,586 A | 3/1976 | McKee, Jr. ............ | 75/66 |
| 4,290,822 A | 9/1981 | Maupre et al. ............ | 134/19 |
| 4,403,500 A | 9/1983 | LeBaud ............ | 73/19 |
| 4,549,032 A | 10/1985 | Moeller et al. ............ | 585/445 |
| 4,581,200 A | 4/1986 | Himeno ............ | 376/310 |
| 4,677,237 A | 6/1987 | Imai et al. ............ | 585/444 |
| 4,713,214 A | 12/1987 | Dumay et al. ............ | 376/312 |
| 4,880,764 A | 11/1989 | Imai et al. ............ | 502/326 |
| 5,087,792 A | 2/1992 | Cottrell et al. ............ | 585/661 |
| 5,130,106 A | 7/1992 | Koves et al. ............ | 422/216 |
| 5,405,586 A | 4/1995 | Koves ............ | 422/218 |
| 5,525,311 A | 6/1996 | Girod et al. ............ | 422/200 |

FOREIGN PATENT DOCUMENTS

| | | |
|---|---|---|
| DE | 2028297 | 12/1971 |
| GB | 2170898 | 8/1986 |

*Primary Examiner*—Nadine Preisch
(74) *Attorney, Agent, or Firm*—John G. Tolomei; Frank S. Molinaro; Mark Goldberg

(57) ABSTRACT

A process for using a hydrogen sensor in a liquid metal heat exchange loop in a hydrocarbon conversion process with high hydrogen permeation. The hydrogen sensor of the present invention consists essentially of a hollow nickel membrane probe in intimate contact with liquid metal. A vacuum chamber in fluid communication with the hollow nickel membrane probe through which hydrogen permeates, wherein the vacuum chamber is initially evacuated to a vacuum pressure and is in equilibrium with the vacuum chamber. The hydrogen sensor is useful for measuring the partial pressure of the hydrogen in the liquid metal to provide advisory control for the removal of hydrogen from the liquid metal exchange loop to avoid the problem of metal hydride formation and associated plugging problems.

14 Claims, 2 Drawing Sheets

PROCESS FOR DETECTING IMPURITIES IN LIQUID METAL HEAT EXCHANGE FLUID IN HIGH HYDROGEN PERMEATION ENVIRONMENT

FIELD OF THE INVENTION

This invention relates to the use of liquid metals as an indirect heat exchange fluid to indirectly heat or cool fluids containing high concentrations of hydrogen.

BACKGROUND OF THE INVENTION

Liquid metal heat exchange systems have been generally used in the nuclear industry where characteristically high temperature differences between the heat source and the cooling medium require the use of a heat transfer fluid which will not change phase at any point in the heat exchange circuit. Such systems have been primarily used as a cooling medium in fast breeder nuclear reactors wherein heat build-up on the reactor side of the heat exchange equipment can occur quickly and it is required to remove this heat with a heat transfer fluid which remains a liquid over the full range of temperature.

In many industries, like the petrochemical and chemical industries, contact of reaction fluids with a catalyst in a reactor under suitable temperature and pressure conditions effects a reaction between the components of one or more reactants in the fluids. Most of these reactions generate or absorb heat to various extents and are, therefore, exothermic or endothermic. The heating or chilling effects associated with exothermic or endothermic reactions can positively or negatively affect the operation of the reaction zone. The negative effects can include among other things: poor product production, deactivation of the catalyst, production of unwanted by-products and, in extreme cases, damage to the reaction vessel and associated piping. More typically, the undesired effects associated with temperature changes will reduce the selectivity or yield of products from the reaction zone.

Many arrangements seek to overcome the negative effects of endothermic chilling by supplying heat to the reaction or of exothermic heating by removing heat from the reaction. More traditional methods employ multiple stages of heating between adiabatic reaction stages. Other methods use in-situ heating via simultaneous reactions or indirect heat exchange to maintain an isothermal or other temperature profile within the reaction zone. U.S. Pat. No. 5,525,311 provides an example of indirect heat exchange with a heat exchange fluid to control the temperature profile within a reaction zone.

A variety of processes can employ indirect heat exchange within a reaction zone to control temperature profiles within the reaction zone. Common examples of hydrocarbon conversion reactions include the aromatization of hydrocarbons, the reforming of hydrocarbons, the dehydrogenation of hydrocarbons, the oxidation of hydrocarbons and the alkylation of hydrocarbons. Most of these hydrocarbon conversion processes process streams having high concentrations of hydrogen.

It is known to accomplish indirect heat exchange for processes with a variety of heat exchanger configurations including shell and tube heat exchange designs or thin plates that define reaction and heat exchange channels. In such arrangements the tubes typically contain catalyst while the channels contain a heat exchange fluid or in a plate arrangement the channels alternately retain catalyst and reactants in one set of channels and a heat transfer fluid in adjacent channels. Heat exchange plates in these indirect heat exchange reactors can be flat or curved and may have surface variations such as corrugations to increase heat transfer between the heat transfer fluids and the reactants and catalysts. A specific arrangement for heat transfer and reactant channels that offers more complete temperature control can again be found in U.S. Pat. No. 5,525,311, the contents of which are hereby incorporated by reference. Other useful plate arrangements for indirect heat transfer are disclosed in U.S. Pat. No. 5,130,106 and U.S. Pat. No. 5,405,586.

High heat capacity heat transfer fluids are used in several industries to provide cooling for shell and tube heat exchanger arrangements. Various types of high heat capacity fluids include alkali liquid metals such as sodium, lithium, and potassium and include molten salts such as nitrates and carbonates. These heat transfer fluid combine high heat capacity with high thermal conductivity. GB-2170898 generally discloses the use of sodium as a heat transfer medium in high temperature reactions including heat recovery from furnace installations, high pressure nuclear reactors, coal gasification, coal conversion, and water disassociation. U.S. Pat. No. 4,549,032 discloses the use of molten salt as an indirect heat transfer medium with a dehydration of styrene. German patent DE 2028297 discloses the use of an alkaline metal as a heat transfer medium in a process for producing alkenes and aromatics by cracking aliphatic hydrocarbons. The liquid metals are specifically used due to their high heat transfer capacity that permits utilization of small heating surfaces.

When indirectly heating or cooling hydrocarbons or other chemical feeds, the presence of hydrogen poses special problems for the use of liquid metals and other high heat capacity heat transfer fluids. Any finite hydrogen activity requires some provision for removal of metal hydride that will form from hydrogen that constantly permeates through the walls of the barrier between the fluids. Should the metal hydride concentration exceed solubility limits, the precipitation of solid hydride can interfere with the operation of the process or cause damage to equipment. Where the hydrogen permeation rate is small a chemical sorbent or getter material is used to chemically react and bind the hydrogen to prevent saturation of the metal hydride and its subsequent precipitation into the circulating system. Also the nuclear industry has used cold traps for many years to removal small quantities of sodium hydride.

Many hydrocarbon and petrochemical processes have a much higher hydrogen partial pressure on the process side of the heat exchange surfaces than the usual processes in which liquid sodium and other heat transfer fluids have been used. In many hydrocarbon conversion processes, the problem of hydrogen permeation can be severe. Many such processes work best with a relatively high hydrogen partial pressure which directly influences the problem of hydrogen permeation. Furthermore, obtaining a highly efficient heat exchange benefits from an increase in the surface area for the indirect heat exchange. As a surface area increases relative to the flowing fluid volume, the permeation of hydrogen into the liquid metal also increases. The recent trend in heat exchange arrangements for hydrocarbon conversion processes is to use a series of thin stacked plates which maximizes surface area, but at the same time, greatly increases the hydrogen permeation rate, particularly for those processes that maintain a relatively high hydrogen-to-hydrocarbon ratio. When hydrogen migrates into the liquid metal heat exchange fluid, the hydrogen forms the compound, sodium hydride. At low concentrations, the sodium hydride is soluble in the liquid metal heat exchange fluid, however, as the concentration of sodium hydride reaches a critical level, the sodium hydride begins to form a solid participate on the walls of the heat exchange surface, reducing the efficiency of the heat exchange process and if allowed to continue actually stopping the process.

Therefore, it is particularly desirable to have a process that can simply and effectively detect the concentration of hydrides in the liquid metal heat exchange fluid before the concentration of the hydrides reaches a critical level. Prior attempts to monitor the hydride level in liquid metal heat exchange systems employed very elaborate detection systems operating at very low vacuum conditions. For example, U.S. Pat. No. 4,403,500 discloses an apparatus for measuring hydrogen leaks in a liquid sodium heat exchange system in a steam generator of a fast breeder nuclear reactor. The device includes a technique for employing a single vacuum pump and a selector to maintain one or more measuring chambers at ultra high vacuum conditions and employing signals emitted by a mass spectrometer processed in a calculator unit to determine the equivalent hydrogen partial pressure in each of the chambers. The pressure in the chamber is maintained at about $10^{-7}$ to $10^{-8}$ torr. The hydrogen pressure is determined by Sievert's law and the presence of hydrogen is used to indicate the presence of a water leak in the cooling coil of a nuclear reactor.

U.S. Pat. No. 3,731,523 discloses the use of a hollow nickel probe which is evacuated by an ion pump to a pressure of $10^{-6}$ torr to measure hydrogen concentrations in sodium-cooled nuclear reactors. Nuclear reactors will have a normal hydrogen concentration level in the range of 0.1 to 2.0 ppm. Accordingly, the ion pump is turned off and the probe is inserted into a liquid sodium conduit. Hydrogen diffuses through the nickel and is allowed to reach an equilibrium pressure inside the probe. The pressure change in the probe is measured and Sievert's law is applied to determine the hydrogen concentration in the sodium metal stream and to indicate the presence of a water leak in the cooling coil of a nuclear reactor. The ion pump is employed to re-evacuate the nickel probe for each measurement to detect hydrogen concentration of at least 0.1±0.01 ppm. When such methods are employed to determine water leaks, they must be extremely sensitive to very small hydrogen concentration changes and detect such changes rapidly.

Typical cold traps that remove hydride precipitate or getters would quickly reach their capacity limit with the high hydrogen permeation rates associated with the chemical process. Replacement of cold traps and getter material will be prohibitively costly and inconvenient.

Those skilled in the art of using liquid metals as indirect heat exchange materials have addressed the problem of eliminating impurities, in particular, hydrides from the liquid metal streams. U.S. Pat. No. 4,713,214 shows a degassing chamber for purifying liquid metal coolant from a fast neutron nuclear reactor using a filter element that provides the primary means of purification and a degassing chamber that collects bubbles of an inert gas blanket that may become entrained in the circulating liquid sodium. U.S. Pat. No. 4,581,200 uses a tank in combination with a cold trap wherein the tank deposits a sodium mist in contact with hydrogen to act as a hydrogen getter for subsequent intermediate release of hydrogen by heating of the sodium deposit. U.S. Pat. No. 4,290,822 discloses a method for cleaning a cold trap that uses sodium hydroxide to transform heated impurities into liquid phase and then draining off the liquid phase that may use vacuum conditions to remove any possible traces of water. U.S. Pat. No. 3,941,586 also teaches the purification of cold trap by heating sodium hydride to a molten state and removing or venting hydrogen gas from the cold trap. The typical apparatus associated with a cold trap comprises an economizer exchanger that transfers heat between hot, unpurified metal and the cold purified metal, a cooler for the liquid metal, and some form of retainer for a filtering element, or metallic fibers. It is known from U.S. Pat. No. 4,713,214 that cold trap devices may be integrated in a reaction vessel or may be external to the reaction vessel and involve a secondary circulation loop. U.S. Pat. No. 4,290,822 discloses the heating of cold traps with resistance heaters to maintain a temperature of about 355° C. to dissolve sodium hydride and sodium hydroxide. None of these methods are particularly suited for process fluids that have a high hydrogen concentration.

It is, therefore, an object of this invention to provide a method of detecting hydride from circulating liquid metal heat exchange fluids that can accommodate a high hydrogen permeation from the process fluid.

It is a further object of this invention to provide a simplified system of detecting and providing advisory control for removing hydrogen and the resulting metal hydride from a circulating liquid metal heat transfer fluid that facilitates the regeneration of traps for further purification of the circulating liquid metal material.

BRIEF SUMMARY OF THE INVENTION

This invention is a process for the use of a hydrogen sensor to be used with liquid metal heat exchange fluids in a process that has a high hydrogen permeation. It was surprisingly discovered that at the high levels of hydrogen which migrate into a liquid metal heat exchange loop in a hydrocarbon conversion process, such processes can employ a simplified hydrogen sensor to effectively report the high hydrogen partial pressure levels in the liquid metal stream without the need to re-evacuate the sensor between determinations. Furthermore, it was found that the rate of change of the hydrogen partial pressure was sufficiently rapid enough to employ the hydrogen partial pressure reported to manage the liquid metal stream between heat exchange service and regeneration for hydrogen removal.

Accordingly, in one embodiment, the present invention is a process for using a hydrogen sensor in a hydrocarbon reaction zone. The hydrocarbon reaction zone operates under hydrogen partial pressure while indirectly exchanging heat with a liquid metal stream that circulates in a heat exchange loop. A portion of the hydrogen from the reaction zone migrates across a heat exchange surface into a recirculating liquid metal stream in the heat exchange loop. At least a portion of the recirculating liquid metal stream is passed to a hydrogen removal zone and returned to the recirculating liquid metal stream. Intimate contact with at least a portion of the recirculating metal stream and a hollow nickel membrane probe of a hydrogen sensor is provided. The hydrogen sensor comprises: a hollow cylinder containing the hollow nickel membrane probe; a vacuum chamber in fluid communication with the hollow nickel membrane probe; and a pressure transducer, establishing equilibrium between the hydrogen that passes through the nickel membrane probe to the vacuum chamber and the hydrogen in the recirculating liquid metal stream. The hydrogen sensor is operated at effective sensor conditions to measure hydrogen partial pressure in the vacuum chamber over a hydrogen partial pressure range of about 2 to about 10 mm Hg.

DETAILED DESCRIPTION OF THE INVENTION

Figure 1:
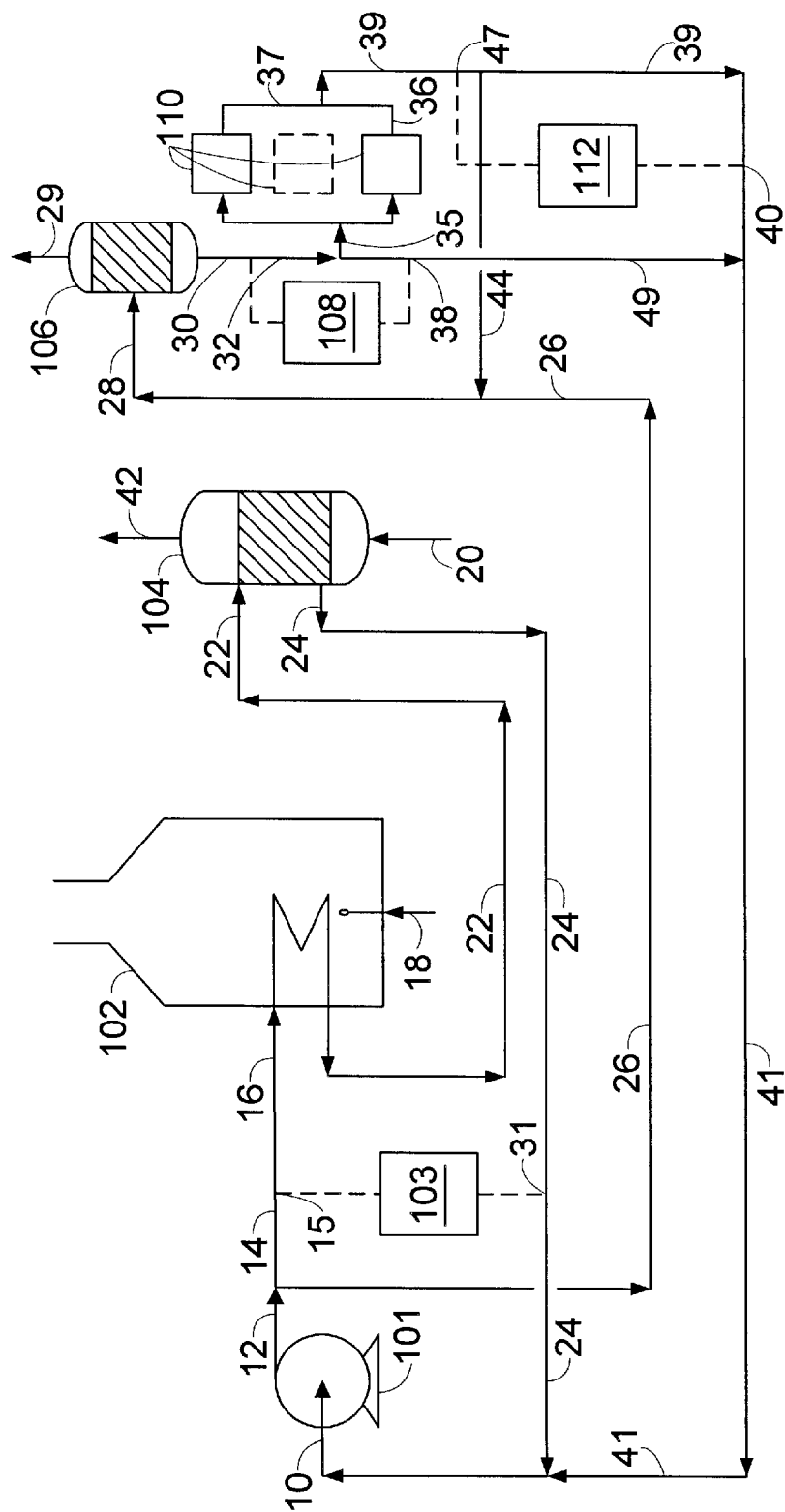
FIG. 1 is a schematic flow diagram of an arrangement of the invention.

Suitable heat exchange fluids comprise metals that maintain a liquid state at the desired heat exchange conditions of the process. Preferably, the molten metal is selected from the group consisting of sodium, potassium, lithium, lead, antimony, bismuth, and mixtures thereof. Mixtures of the above metals may form particularly useful eutectic mixtures.

The method may be useful in a wide variety of catalytic processes that use homogeneous or heterogeneous catalysts. This invention is most beneficially applied to catalytic conversion processes having high heats of reaction that process or produce streams containing molecular hydrogen. Typical reactions of this type are hydrocarbon conversion reactions that include the aromatization of hydrocarbons, the reforming of hydrocarbons, the dehydrogenation of hydrocarbons, and the alkylation of hydrocarbons. More specific hydrocarbon conversion processes to which this invention is suited include catalytic dehydrogenation of paraffins, reforming of naphtha feedstreams, aromatization of light hydrocarbons, and the alkylation of aromatic hydrocarbons. This method is particularly beneficial for endothermic processes such as dehydrogenation and reforming. This invention is most advantageously used in processes where the hydrogen partial pressure is at least 15 psia in the stream that is indirectly heated or cooled by the liquid metal and is more preferably used in processes where the hydrogen partial pressure of the process stream is 25 psia or greater.

Looking further at the catalytic dehydrogenation of paraffins as an example of an endothermic process, feedstocks ordinarily have from about 3 to about 18 carbon atoms. Particular feedstocks will usually contain light or heavy paraffins. The feedstock is admixed with a recycle stream comprising hydrogen and contacted with catalyst in a reaction zone. A catalytic dehydrogenation reaction is normally effected in the presence of catalyst particles comprised of one or more Group VIII noble metals (e.g., platinum, iridium, rhodium, and palladium) combined with a porous carrier such as a refractory inorganic oxide. Alumina is a commonly used carrier. Dehydrogenation conditions include a temperature of from about 400° to about 900° C., a pressure of from about 0.01 to 10 atmospheres, and a liquid hourly space velocity (LHSV) of from about 0.1 to 100 $hr^{-1}$. Generally the lower the molecular weight of the feed the higher the temperature required for comparable conversions. The pressure in the dehydrogenation zone is maintained as low as practicable, consistent with equipment limitations to maximize the chemical equilibrium advantages. The preferred dehydrogenation conditions of the process of this invention include a temperature of from about 400° to 700° C. and a pressure from about 0.1 to 5 atmospheres.

The effluent stream from a dehydrogenation zone generally will contain unconverted dehydrogenatable hydrocarbons, hydrogen, and the products of dehydrogenation reactions. This effluent stream is typically cooled and passed to a hydrogen separation zone to separate a hydrogen-rich vapor phase from a hydrocarbon-rich liquid phase. Unconverted dehydrogenatable hydrocarbons are recovered and may be recycled to the dehydrogenation zone. Products of the dehydrogenation reactions are recovered as final products or as intermediate products in the preparation of other compounds. Additional information related to the operation of dehydrogenation catalysts, operating conditions, and process arrangements can be found in U.S. Pat. No. 4,677,237, U.S. Pat. No. 4,880,764, and U.S. Pat. No. 5,087,792, the contents of which are hereby incorporated by reference.

The hydrogen removal zone uses a degassing zone for the removal of hydrogen from the liquid metal heat exchange stream by decomposition of the metal hydride from the circulating metal stream. Normally the degassing zone will treat a smaller side stream or slipstream that equal about 1 to 5 percent of the total circulating stream and preferably equals 1 to 2 percent of the circulating stream. The degassing zone will usually be maintained at a temperature of not less than about 300° C. While there is no limit on the upper temperature for the heating of the liquid metal for hydride decomposition, practical design considerations will limit the temperature to not more than about 540° C. In general, the temperature in the degassing zone will be maintained in the temperature range of the heat transfer fluid in the process. Passage through the degassing zone will reduce the hydrogen concentration in the liquid metal to near equilibrium levels. For the preferred vacuum conditions of the degassing zone and the preferred liquid sodium heat transfer fluid, the effluent from the degassing zone will have sodium hydride level of between 50 to 250 ppm and preferably a hydride level of less than 150 ppm. The degassing zone will usually be maintained at a vacuum of from 1 to 10 mm Hg and a preferred vacuum condition of from 2 to 5 mm Hg and more preferably from 2 to 3 mm Hg. The preferred temperature for the degassing zone will be at a temperature of from 400° to 550° C. Residence time for the liquid sodium within the degassing zone will typically range from 2 to 5 minutes.

To further reduce the hydride level, the purified liquid metal from the contacting vessel passes through one or more cold traps. Those skilled in the art know generally how to design a variety of cold traps that can vary from complex devices to relatively simple filter elements. In typical design and operation, a cold trap passes cooled liquid metal through a filter consisting of metallic fibers which can comprise stainless steel. The hydride precipitates preferentially on the metallic fibers of such filters if the temperature of the liquid metal is sufficiently low. In this manner the devices permit cold trapping of the hydride impurity. The purified stream with approximate equilibrium level of hydride may pass through multiple cold traps in serial flow to reduce the final hydride concentration to desired levels. It is also possible to incorporate additional traps for the removal of other impurities. For example, the temperature of subsequent cold traps in a series may be lowered to a temperature that permits the recovery of precipitated metal oxides. The cold trap is typically maintained at a temperature of 250° C.

DETAILED DESCRIPTION OF THE PREFERRED EMBODIMENTS

The overall process is more fully appreciated from FIG. 1. In brief description, the drawing shows the invention applied to a circulating stream of liquid metal heat exchange fluid. FIG. 1 shows a simplified schematic. This schematic arrangement does not show valves, instrumentation, heat exchangers and other equipment that those skilled in the art will readily recognize as necessary for process control and promoting process efficiency. The liquid metal heat exchange loop consists of passing a recirculating liquid metal stream in line 10 to pump 101 and passing the recirculating liquid metal stream in lines 12, 14, and 16 to heater 102 to add heat to the recirculating liquid metal stream and provide a heated metal stream in line 22. The heated metal stream in line 22 is passed to reaction zone 104 wherein the reactants in line 20 are connected to a reactor effluent stream in line 42 in the presence of a catalyst. Heat is indirectly exchanged between the heated metal stream and the reaction zone to heat the reaction zone and an exchanged metal stream is withdrawn in line 24. The exchanged metal stream in line 24 is returned in line 24 to provide the recirculating liquid metal stream in line 10. A hydrogen sensor 103 permits the passage of a small amount of the recirculating liquid metal stream withdrawn at point 15 on line 14 through the hydrogen sensor 103 and exits via line 24 at point 31. The hydrogen sensor 103 provides a measure of the hydrogen partial pressure in the recirculating liquid metal stream in line 12 which can be related to the amount of hydride dissolved in the recirculating liquid metal stream. The hydrogen partial pressure will range between about 2 and about 10 mm Hg. Preferably, the hydrogen partial pressure is maintained between about 6 and about 8 mm Hg. More preferably, the hydrogen partial pressure is maintained between about 4 and about 6 mm Hg. When the hydrogen partial pressure as measured in hydrogen sensor 103 exceeds about 8 mm Hg, the flow of the slipstream of recirculating liquid metal in line 26 is increased to the degassing zone 106 via lines 26 and 28. In the degassing zone 106, the pressure is reduced to permit a portion of the hydrogen to be vented via line 29 after appropriate steps to prevent release of any vaporized metal. A portion of a circulating stream of liquid sodium is circulated through a process line 10 by a circulation pump 101. A slipstream in line 26 is taken downstream of pump 101 and passed via line 28 to a degassing zone 106. The degassing zone 106 is filled with packing having appropriate size and depth to provide sufficient interfacial surface area and residence time for hydrogen disengagement. A hydrogen vent stream is removed in line 29 and passed to fuel following the removal of any metal vapor. The recovered hydrogen may be vented, used as a fuel, or otherwise recovered.

Purified or degassed liquid sodium may be returned to line 10 via lines 30, 32, 49, and 41 or may direct all or a portion of the stream to one or more cold traps 110 via line 35. In a typical arrangement, 50 percent or more of the purified liquid sodium will return directly to the circulating stream. A network of distribution lines 35 deliver the degassed liquid sodium after chilling to sufficient temperature for precipitation of the metal hydrides to the cold traps 110. A network of collection lines 36 and 37 return the further purified liquid sodium to line 10 via lines 39 and 41.

The degassing zone 106 can serve as part of an integral regeneration system for prolonging the life of cold traps indefinitely. With regeneration the life of the cold trap may be prolonged many times over its usual life expectancy. A second hydrogen sensor 108 monitors the hydrogen partial pressure in line 30 and returns the small amounts of degassed liquid metal stream at point 38 in line 49. Should the second hydrogen sensor 108 indicate an increase in the level or concentration in the degassed liquid metal stream in line 30, the portion of the degassed liquid metal stream passed to the cold traps via line 35 is increased to further reduce the hydrogen level. Similarly, a third hydrogen sensor 112 withdraws a small amount of the trap outlet metal stream in lines 37 and 39 at point 47. If the level of hydrogen is above the desired level, a portion of the trap outlet metal stream in line 39 is passed via line 44 to be degassed in the degassing zone 106. Normally, the flow in line 44 would be significant during a regeneration of one of the cold traps 110.

Figure 2:
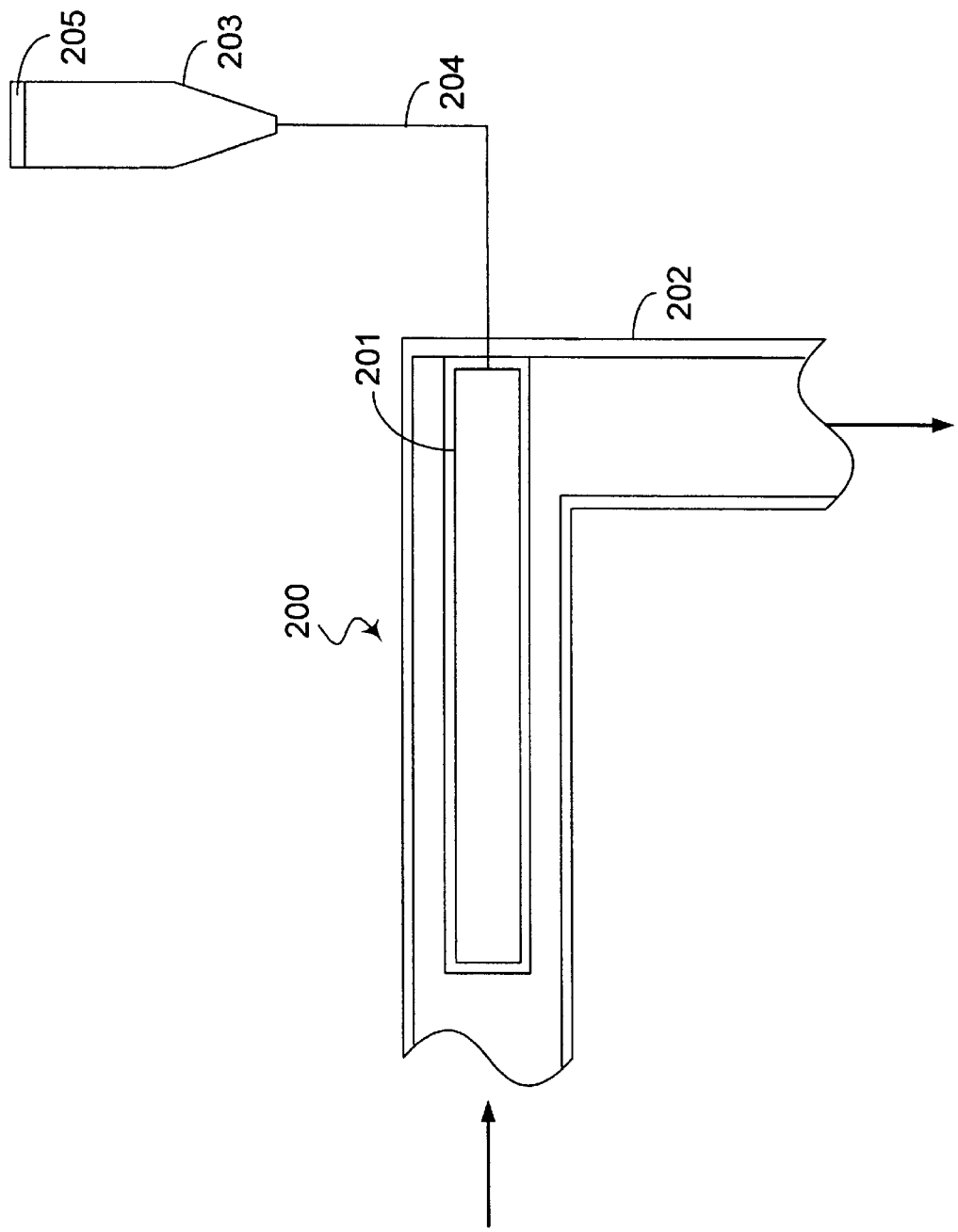
FIG. 2 is a cross-sectional view of the hydrogen sensor.

FIG. 2 shows a cross-sectional view of the hydrogen sensor 200 of the present invention. The hydrogen sensor 200 comprises of a hollow nickel membrane probe 201 rigidly disposed in a tubular shell, or hollow cylinder 202 having an interior zone through which a small slipstream of the liquid metal stream is permitted to flow in intimate contact with the nickel membrane probe. The nickel membrane probe consists of a hollow sealed tube having an interior membrane zone forming at least a portion of a vacuum chamber. The nickel membrane probe is in fluid communication with a vacuum chamber 203 and is connected to the vacuum chamber by a conduit 204. The vacuum chamber incorporates a pressure transducer 205 to electronically report the partial pressure of hydrogen which passes through the nickel membrane probe 201 and remains in equilibrium with the hydrogen in the liquid metal stream. Preferably, the effective sensor conditions include a sensor temperature of about 370° to about 550° C. Prior to placing the hydrogen sensor in service, the vacuum chamber is initially evacuated to a vacuum pressure of about 0.1 to about 10 mm Hg. Surprisingly, it was discovered that the vacuum chamber did not require re-evacuation prior to each determination for the 2 to 10 mm Hg hydrogen partial pressure range of interest. Thus, the hydrogen sensor of the present invention is operated without the use of a vacuum device such as a vacuum pump or ion pump to continuously or intermittently maintain effective sensor conditions.

EXAMPLE

A sealed nickel membrane probe comprising a cylindrical tube of nickel 201 about 165 mm (6.5 inches) in length having a wall thickness of 0.5 mm (0.02 inches) and an inside diameter of about 11 mm (0.432 inches ID). One end of the tube was sealed and the tube was rigidly disposed in a 25-mm (1-inch) 304 stainless steel pipe. The other end of the tube was placed in direct fluid communication with a vacuum chamber by a conduit. The vacuum chamber was equipped with an absolute pressure transducer to directly measure the hydrogen partial pressure in the nickel membrane probe. Initially, the vacuum chamber and the nickel membrane were evacuated to an absolute pressure of about 0.1 mm Hg with a vacuum pump and the vacuum pump was disconnected from the vacuum chamber. The nickel membrane probe was heated to a temperature of about 510° C. and a gas containing about 12,000 ppm-vol hydrogen in argon at a pressure of about 117 kPa (17 psia), (which is equivalent to a sodium hydride concentration in a liquid sodium heat exchange loop of about 380 ppm-wt NaH) was introduced on the outside of the probe at a rate of about 200 cc/minute. The pressure in the vacuum chamber increased to about 6.70 mm Hg in about 140 minutes. At this point, the hydrogen gas composition was changed to about 470 ppm-vol hydrogen in argon at a pressure of 186 kPa (27 psia) which is equivalent to about 95 ppm-wt NaH in solution in a liquid sodium stream. The pressure in the vacuum chamber dropped to about 1.5 mm Hg after about 95 minutes. The switching between the 12,000 ppm-vol hydrogen gas composition and the 470 ppm-vol hydrogen was continued. Surprisingly, the pressure in the vacuum chamber rose to essentially the same level once the same period when the 12,000 ppm-vol stream was introduced and the pressure in the vacuum chamber reduced to the same level on reintroduction of the 470 ppm-vol stream in successive cycles. This indicated that it was not necessary to re-evacuate the vacuum chamber between determinations of hydrogen partial pressure in the nickel membrane probe. This permits the use of relatively inexpensive hydrogen sensors in the chemical reaction and liquid sodium heat exchange loop to measure and control sodium hydride levels in liquid sodium in high hydrogen environments.

What is claimed is:

1. A process for using a hydrogen sensor in a hydrocarbon reaction zone that operates under hydrogen partial pressure while indirectly exchanging heat with a liquid metal stream that circulates in a heat exchange loop wherein a portion of the hydrogen from the reaction zone migrates across a heat exchange surface into a recirculating liquid metal stream, at least a portion of the recirculating liquid metal stream is passed to a hydrogen removal zone and returned to the recirculating liquid metal stream; providing intimate contact with at least a portion of the recirculating metal stream and a hollow nickel membrane probe of a hydrogen sensor comprising a hollow cylinder containing the hollow nickel membrane probe, a vacuum chamber in fluid communication with the hollow nickel membrane probe, and a pressure transducer, establishing equilibrium between the hydrogen that passes through the nickel membrane probe to the vacuum chamber and the hydrogen in the recirculating liquid metal stream; and operating the hydrogen sensor at effective sensor conditions to measure hydrogen partial pressure in said vacuum chamber over a hydrogen partial pressure range of about 2 to about 10 mm Hg.

2. The process of claim 1 wherein the reaction zone contains an endothermic reaction and the recirculating liquid metal stream is heated prior to indirectly exchanging heat with the reaction zone in the hydrocarbon conversion system.

3. The process of claim 1 wherein the vacuum space is initially evacuated to a vacuum pressure greater than about 0.1 mm Hg and less than about 10 mm Hg.

4. The process of claim 1 wherein the effective sensor conditions include a sensor temperature of about 370° to about 550° C.

5. The process of claim 1 wherein the portion of the liquid metal stream that has intimate contact with the nickel membrane probe passes into the hollow cylinder having an interior zone, the nickel membrane probe consisting of a hollow sealed tube having an interior membrane zone forming said vacuum chamber, said nickel membrane probe being rigidly disposed in the interior zone of the hollow cylinder, the vacuum chamber being initially evacuated to a vacuum pressure of about 0.1 to about 10 mm Hg, and a conduit in fluid communication between the nickel membrane probe and the vacuum chamber.

6. The process of claim 1 wherein the nickel membrane probe comprises nickel 201.

7. The process of claim 1 wherein the hydrogen removal system comprises a combination of hydrogen removal techniques selected from the group consisting of degassing, cold traps, and combinations thereof.

8. The process of claim 1 wherein the recirculating liquid metal steam comprises a liquid metal selected from the group consisting of sodium, potassium, and mixtures thereof.

9. The process of claim 1 wherein the portion of the recirculating liquid metal stream passed to the hydrogen removal zone comprises between about 2 to about 5 percent of the recirculating liquid metal stream.

10. The process of claim 1 wherein the portion of the recirculating liquid metal stream passed to the hydrogen removal zone is increased when the hydrogen sensor indicates a hydrogen partial pressure above about 6 to 8 mm Hg.

11. The process of claim 1 wherein the portion of the recirculating liquid metal stream passed to the hydrogen removal zone is increased when the hydrogen sensor indicates a hydrogen partial pressure above about 4 to 6 mm Hg.

12. The process of claim 1 wherein the hydrogen removal zone comprises a degassing zone and a cold trap zone, the process further comprising passing the exchanged liquid stream to the degassing zone to remove at least a portion of the hydrogen to provide a degassed metal stream, measuring the hydrogen partial pressure in the degassed metal stream with a second hydrogen sensor, and combining a portion of the degassed stream with the recirculating metal stream and passing the remaining portion of the degassed metal stream to the cold trap zone to further remove hydrogen by trapping metal hydride and providing a trap outlet metal stream, measuring the hydrogen partial of the trap outlet metal stream in a third hydrogen sensor, and combining a of the trap outlet metal stream with the exchanged metal stream and admixing a of the trap outlet metal stream with the recirculating liquid metal stream.

13. The process of claim 12 wherein the cold trap is periodically regenerated.

14. The process of claim 1 wherein the hydrogen sensor is operated without the continuous or intermittent use of a vacuum pump to maintain effective sensor conditions.

* * * * *